United States Patent [19]

Penrock

[11] 4,024,876
[45] May 24, 1977

[54] PROSTHETIC BRASSIERE

[76] Inventor: William B. Penrock, 4426 Lankershim Blvd., North Hollywood, Calif. 91602

[22] Filed: June 2, 1975

[21] Appl. No.: 583,103

[52] U.S. Cl. .................................. 128/472; 3/36; 128/478; 128/494; 128/510
[51] Int. Cl.² ........................ A41C 3/10; A61F 1/00
[58] Field of Search .......... 128/472, 478, 469, 470, 128/473, 482, 494, 504, 510, 514, 462; 2/DIG. 6; 3/36

[56] References Cited

UNITED STATES PATENTS

| | | | |
|---|---|---|---|
| 2,567,732 | 9/1951 | Rosenthal | 128/478 |
| 2,900,981 | 8/1959 | Herbener | 128/472 X |
| 3,439,682 | 4/1969 | DeFru | 128/510 X |
| 3,528,431 | 9/1970 | Abramo | 128/510 X |
| 3,701,168 | 10/1972 | Balow | 128/478 X |
| 3,763,865 | 10/1973 | DeFru | 128/510 X |

*Primary Examiner*—Werner H. Schroeder
*Assistant Examiner*—Moshe I. Cohen

*Attorney, Agent, or Firm*—Georges A. Maxwell

[57] ABSTRACT

A prosthesis and breast supporting brassiere including a body-encircling breast structure defining a pair of forward upwardly opening breast and/or prosthesis receiving and supporting pockets, resilient spring means yieldingly biasing the portions of the band adjacent the pockets in extended non-folded or unrolled condition, a rearwardly opening breast or prosthesis covering cup forward of each pocket and having a lower edge portion hingedly secured to its related pocket below the upwardly forwardly and downwardly extending upper edge portion thereof, shoulder strap means from the rear of the band to the pocket receiving portion of the band, releasable hook means on and between said strap means and upper edge portions of the cups to normally prevent forward and downward pivoting of the cup relative to the band and a pair of flat panels corresponding in general plane configuration with the open rear of the cups and each selectively removably secured to the band in normal overlying relationship to the open rear of one of the cups.

4 Claims, 9 Drawing Figures

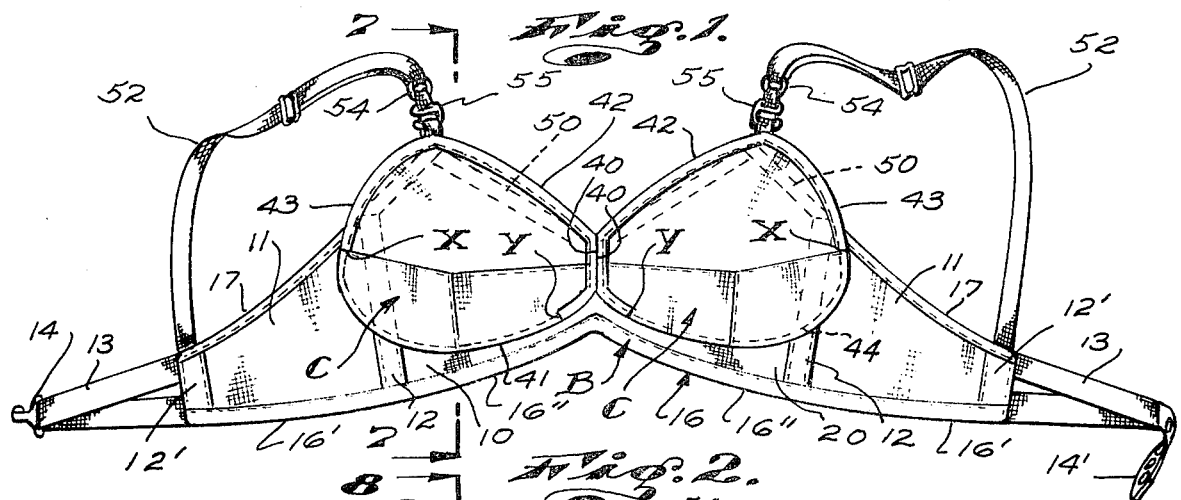
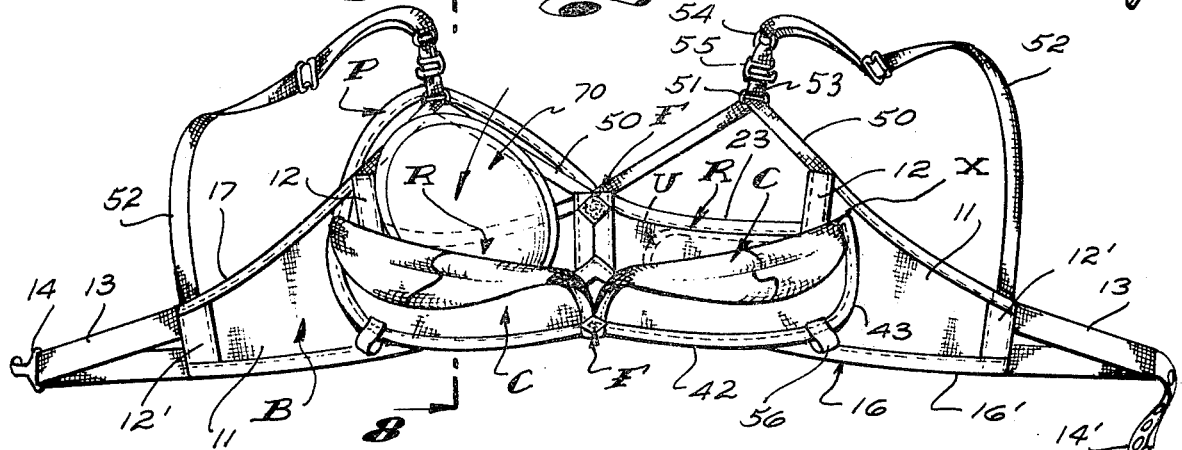
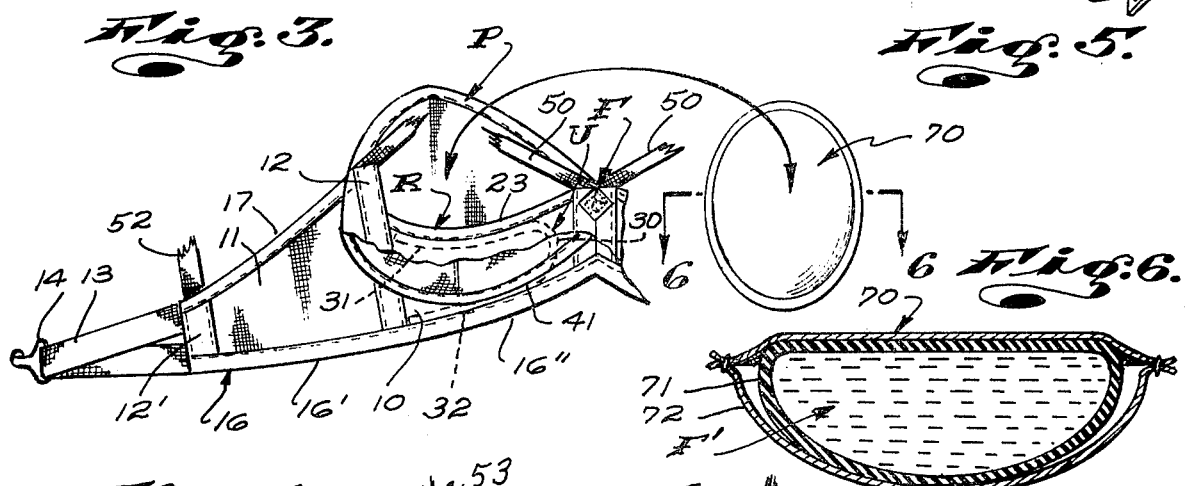
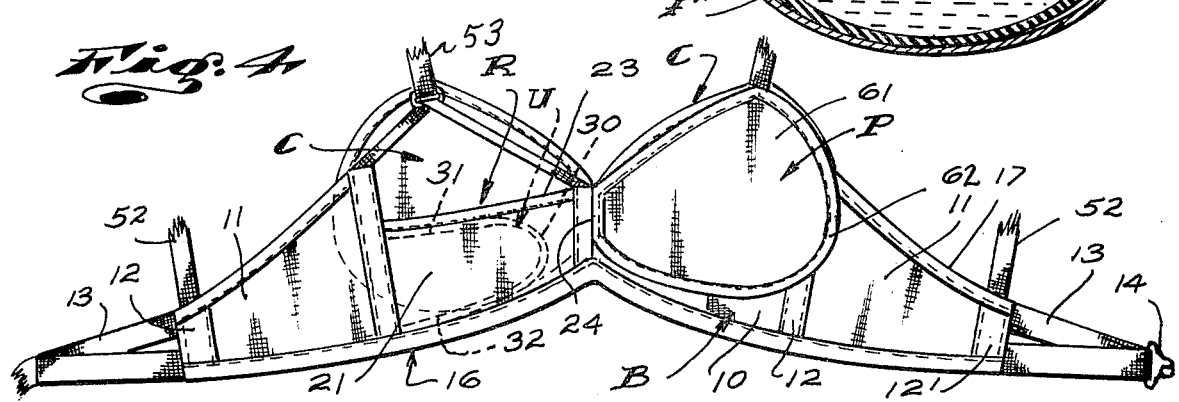

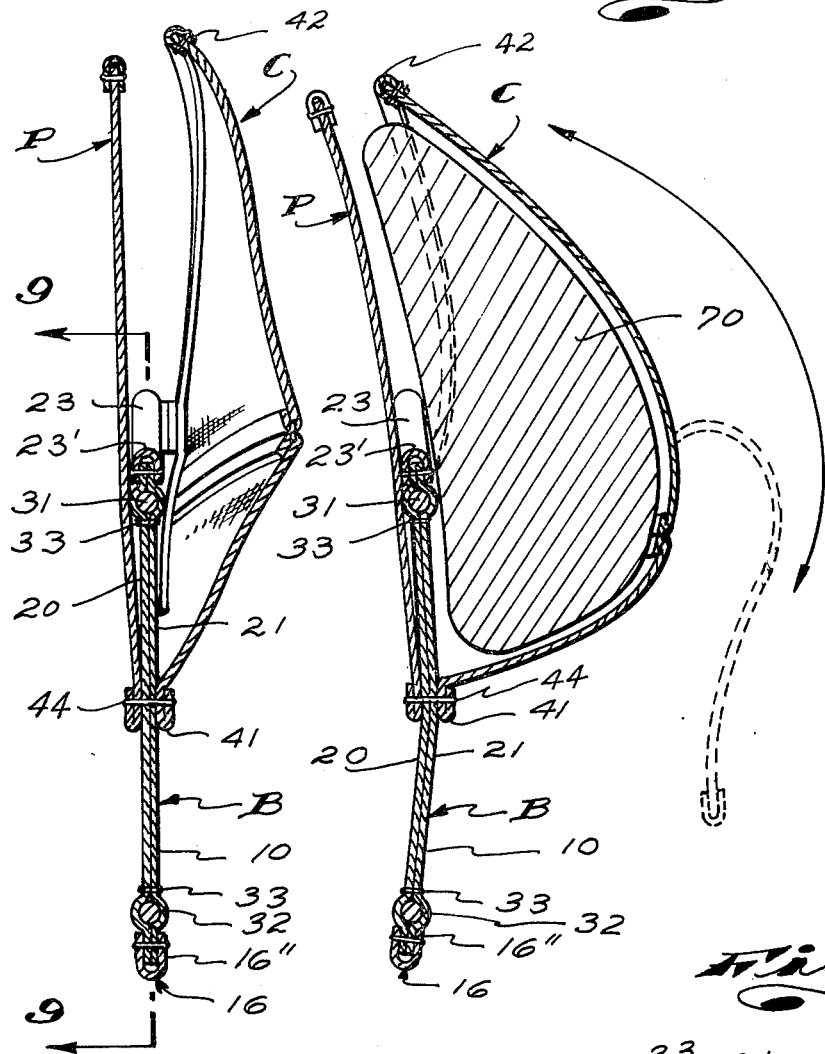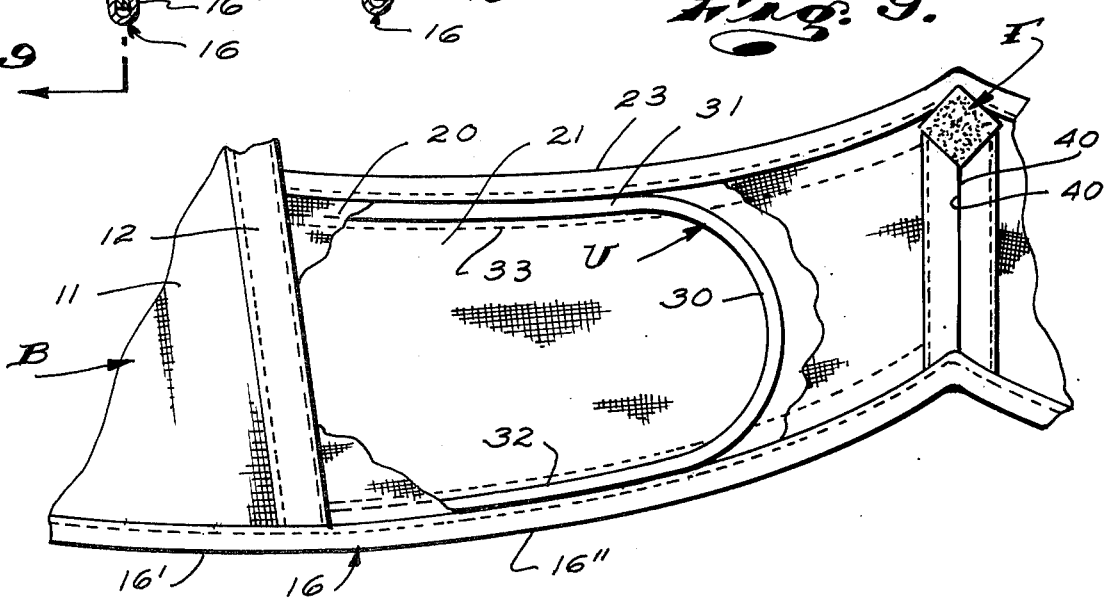

PROSTHETIC BRASSIERE

This invention has to do with a brassiere and is more particularly concerned with a brassiere structure for prosthetic breasts.

It is not uncommon for women to be subjected to mastectomy, that is, the surgical removal of one or both breasts. Women subjected to such surgery are often severely physically disfigured and are frequently left psychologically and emotionally disturbed. Rather basically, they are often left to feel and believe that they are less than whole, less feminine and therefore less socially acceptable.

In order to compensate for the physical loss suffered by such woman and to make them outwardly appear whole, feminine and therefore socially acceptable, it is common practice to provide them with prosthetic breasts.

In the past, prosthetic breasts were established of lightweight pillow-like cushions filled with fibrous padding material, such as cotton. Such prosthesis were often very obviously artificial looking, were of very questionable effectiveness and have become quite unacceptable by those in need of such devices.

The principal shortcomings to be found in fiber-filled prosthetic breasts of the nature referred to above resides in the fact that they are considerably lighter than a normal breast and fail to provide that balance and distribution of weight which is required to afford the user a natural appearance. Further, such prosthesis are rather rigid, non-fluid, non-ductile or non-plastic in nature and not only fail to settle and distribute their mass in the manner that natural breasts do (under the force of gravity), but fail to flow about and redistribute their mass in a regular and natural appearing manner when women wearing them walk or otherwise move about in the course of day-to-day activities.

As a result of the above and in an effort to establish and provide more natural appearing prosthetic breasts, the art to which this subject matter relates provides prosthetic breasts which are substantially equal in size, weight and shape as the breasts they serve to replace and which are substantially the same as the breasts as regards softness, fluidity, ductility and/or plasticity.

To the above end, the present day prosthetic breast is generally and/or most often characterized by a thin-walled flexibly and somewhat elastic molded plastic, sealed, envelope or vessel in the general form or configuration of the breast it is made to simulate and is filled with that volume of water or other suitable fluid necessary to impart into it the necessary or desired weight and volume or fullness.

While the above practices are quite effective to establish and realistic prosthetic breasts, the prosthesis are most often quite heavy, weighing several pounds and are so fluid, ductile and/or plastic in nature that they are not easily handled.

The upper, inside or rear portion of a wearer's breast is to a substantial extent supported and held up by its joinder to the body or rib cage and a brassiere provides desired under and outside support for the lower, forward and/or outer portion of the breast. Further, the breast is naturally permanently oriented relative to the body or rib cage.

In the case of a prosthetic breast, the prosthesis finds no vertical support and no sure orientation from or by the body of the wearer and is free to drop downwardly and out of desired orientation, but for the brassiere which is provided to hold and support it. Accordingly, a brassiere must provide substantially total support and containment for the typical prosthetic breast whereas in the case of a natural breast, the support and containment it provides is only supplemental to the natural support and orientation afforded by the body.

As a result of the foregoing, while quite natural looking and acting prosthetic breasts are available, great difficulty is experienced in properly and effectively containing and supporting them by means of ordinary brassieres. When using ordinary brassieres to support prosthetic breasts, there is a tendency for the prosthesis to drop and pull the brassiere down, to migrate downwardly and drop from between the brassiere and the body of the wearer and/or to shift laterally and/or to rotate or turn about and out of position and orientation within the brassiere. As a result, such ordinary brassieres cannot be effectively and safely used to support and contain prosthetic breasts.

The above has resulted in the establishment and provision of special prosthetic breast brassieres which, as a general rule, are heavy, or bulky, un-feminine, harness-like structures which are most often uncomfortable to wear and which are so aesthetically unattractive and displeasing as to cause emotional stress to the women who must wear them.

The most common characteristic of the prosthetic breast breassiere provided by the prior art is the provision of a broad, heavy, tightly fitting band which extends about the rib cage of the wearer to occur below the lower breast line and which is such that it will not be shifted and/or rolled downwardly by the weight of a prosthetic breast applied thereto and which is such that a prosthesis breast cannot migrate downwardly, between it and the body of the wearer. The noted band is sought to be made heavy enough and is intended to be drawn taut enough so that it is not excessively subject to rolling and/or gathering up into a thin, stiff, narrow cord-like mass. The noted band characteristically extends across and establishes pressure bearing engagement on the solar plexus of the wearer, which pressure, after a short time, results in considerable discomfort.

The ordinary prosthetic breast brassiere is next characterized by substantially standard or usual laterally spaced, forwardly projecting, rearwardly opening, truncated, substantially conical fabric cups with lower edges fixed to the upper edge of the aforementioned band; by shoulder strap fixed to and extending between the upward rear portions of the cups and rear portion of the band and a substantially flat, vertical rear panel of soft fabric fixed with and overlying the lower rear portions of the cup or cups with which the prosthesis or prostheses are to be related and cooperating with the cup or cups to define pockets appearing at the upper rear portions of the cup or cups and in which the prosthesis is to be deposited.

Basicaly, or fundamentally, the above noted common prosthetic breast brassiere can be said to be little more than an extra heavy duty, strictly utilitarian piece of equipment which is rugged and durable in use, requires rugged and often difficult physical manipulation and handling and requires a durable body and a rugged attitude or disposition on the part of the wearer, to cope with it.

In use of the above noted common prosthetic brassiere, the garment is engaged on the wearer before the prostheses are related to it. When the brassiere is in position, the wearer must then manually stuff the prostheses into the cups and thereafter seek to properly orient them within the cups, as by use of her fingers. As a result of physical weakness and the like caused by the mastectomy, the above noted task is often extremely difficult or impossible.

An object and feature of my invention is to provide a novel prosthetic breast brassiere which is light-weight, reasonably brief and quite feminine in design and which is both easy to use and comfortable to wear.

It is another object and feature of this invention to provide a brassiere of the character referred to which includes a novel, light-weight, soft and flexible body engaging band structure with means related to the portions thereof adjacent to the cups to provide yielding support for prostheses or a breast arranged within the cups and which serves to prevent rolling and/or folding of the band beneath and under the weight load of the prostheses or of a prosthesis and a breast.

Yet another object and feature of the present invention is to provide weight distributing and supporting means in the body engaging band portion of a brassiere, as set forth above which is spaced from and clear of the solar plexus of the wearer and such that forces conducted therethrough are directed away from the solar plexus of the wearer.

Still further, it is an object and feature of my invention to provide a brassiere of the character referred to wherein the cup portions are releasably held in a normal up or working position and are such that they can be released and folded forwardly and downwardly to provide easy access to their interior, for easy and convenient engagement and disengagement of prostheses therein, when the brassiere is worn by its user.

The foregoing and other objects and features of my invention will be fully understood and will be apparent from the following detailed description of a preferred form and carrying out of my invention, throughout which description reference is made to the accompanying drawings, in which:

FIG. 1 is a front elevational view of a brassiere embodying the present invention;

FIG. 2 is a view similar to FIG. 1 showing the cups in another position and a prosthesis in position;

FIG. 3 is a view of a portion of the structure shown in FIG. 2 with parts broken away and with the prosthesis removed;

FIG. 4 is a rear elevational view of the structure;

FIG. 5 is a front elevational view of the prosthesis;

FIG. 6 is an enlarged detailed sectional view taken as indicated by line 6—6 on FIG. 5;

FIG. 7 is an enlarged sectional view taken substantially as indicated by line 7—7 on FIG. 1;

FIG. 8 is an enlarged sectional view taken substantially as indicated by line 8—8 on FIG. 2; and FIG. 9 is a view taken as indicated by line 9—9 on FIG. 7.

Referring to the drawings, the brassiere that I provide includes a torso or body encircling the lower band B having a front panel 10 and side panels 11.

The side panels 11 have lateral outer forward ends secured to their related opposite ends of the front panel 10 as by a vertically stitched seam structure 12 and have suitably finished rear central ends 12' adapted to occur in laterally spaced, opposing relationship near the center of the wearer's back. The rear center has looped elastic straps 13, each engaged with and carrying elements 14 and 14' of a conventional, releasably engageable, adjustable loop and eye coupling means C. The means C is adapted to be coupled or made up at the center of the wearer's back and to close the band snugly about the wearer's body, at a level or substantially horizontal plane below the lower breast line of the wearer.

The lower edge 16 of the band B is defined by a finished binding (also identified by the reference numeral 16) sewed thereto. The end portions 16' of the lower edge 16 are defined by the side panels 11 extending substantially horizontally about the adjacent related portions of the wearer's torso. The upper edges 17 of the side panels 11 defined by finished bindings or hems (also identified by reference number 17) diverge relative to the lower edge 16, from the rear central ends 12' thereof in upwardly curved lines toward their related lateral forward ends and to the upper ends of the seams 12.

The panel 10 includes front and rear layers or plies of fabric 20 and 21 and extends transversely between the seams 12. The panel 10 has opposite (right and left) lower edge portions 16" finished and defined by portions of the aforementioned binding 16 and which continue or extend inwardly from the lower ends of their seam 12, upwardly and laterally inwardly to the central front portion of the band where they converge. The upper edge of the panel 10 is defined by a finished binding 23 and has opposite (right and left) portions 23' which extend laterally inwardly from their related seams 12 from points spaced between the upper ends of the seams, to the central portion of the band, where they join. The opposite edge portions 23' are curved slightly downwardly and thence upwardly as they continue laterally inwardly from their related seams 12 and so that they present upwardly disposed slightly concavely disposed edges which occur along the two (left and right) lower breast lines of the wearer when the structure is in use and which converge or meet and establish an upwardly disposed central apical point on the band.

In practice, the front panel 10 can be established of left and right sections joined together at the central portion of the band by a central vertical stretched seam 24, as shown in the drawings, or can be a single unit, from seam 12 to seam 12.

The curvature and relationship of the edges 16" and 23' of the panel 10 are such that the central portion of the panel and/or the seam 24 are of limited vertical extent and are of substantially less vertical extent than the lateral outer vertical edge portions of the panel, at and along the seams 12.

The edges of plies 20 and 21 of the panel 10 are closed and sealed by their related bindings and/or seams to define a sealed interior compartment or compartments.

Arranged and enclosed between the plies and in the compartment or compartments of the panel 10 are a pair of U-shaped resilient load supporting and distributing members U each with a curved or rounded, vertically extending base portion 30 and normally straight, horizontal, upper and lower legs 31 and 32. The members U are arranged between the plies 20 and 21 with their upper and lower legs in biased pressure sealed engagement in and along the upper and lower edges 23' and 16" of their related left and right portions of the panel and with their curved, vertically extending base portions 30 arranged in oppositely and laterally, outwardly disposed relationship and in lateral outwardly spaced relationship from the central portion of the band. The outer free ends of the legs 31 and 32 of the members V stop at the seams 12 and extend laterally inwardly therefrom. In practice, the legs 31 and 32 can be engaged within and contained by the finished bindings on their related edges of the panel 10 or can, as shown, be retained in position in the panel by suitable stitching 33, as shown in FIGS. 7 and 8 of the drawings.

The units U are in essence U-shaped springs and are preferably established of a suitable plastic rod or monofilament of suitable weight, strength and resiliency.

The U-shaped units or springs U serve to yieldingly urge and maintain portions of the panel 10 in which they are arranged, spread in a flat vertical condition and prevent the panel 10 from rolling, folding and/or collapsing vertically when in use. By yieldingly maintaining the panel 10 spread and vertically flat, maximum and substantially uniform area contact is maintained between the panel and the wearer's body, assuring uniform and comfortable distribution of forces on the wearer's body and maximum gripping and/or frictional contact, whereby relative vertical shifting and/or displacement of the panel relative to the body is unlikely to occur.

The above ends are attained without imparting rigidness and/or stiffness to the panel 10 which would impair mobility and flexure of the wearer's body or which might cause discomfort, as has been the case where vertical stays have been employed to impart vertical stability to such panels and as has been the case where the panels have simply been made heavy and stiff enough, as a whole, to assure vertical stability.

It is further important to note that the central portion of the panel is of minimum vertical extent and is indirectly reinforced or supported by the springs U, which springs are spaced laterally outwardly therefrom.

As a result of the above, the central portion 22, which extends across and bears upon the solar plexus of the wearer is soft, pliable and flexible and is such that it does not direct or distribute undesirable and potentially discomforting forces upon the solar plexus region of the wearer's body. In fact, and it should be presently noted that the U-shaped members or springs U are such that vertical forces applied thereto and/or absorbed and handled thereby are directed to and transmitted laterally outwardly away from the central portion of the panel 10 and toward the opposite outer ends of the panel, toward which the legs of the springs project and to which said legs extend.

The brassiere here provided next includes forwardly projecting, rearwardly opening breast and/or prosthesis receiving outer covers or cups C, there being right and left cups related to and overlying the right and left portions of the front panel 10. The cups C are soft, flexible fabric assemblies of the above noted general and desired conical form and are characterized by adjacent joined or stretched together central vertical edges 40 to define a central vertical seam and establish the center of the cup assembly, laterally outwardly extending, downwardly and thence upwardly curved, lower rear edges 41 continuing laterally outwardly from the lower ends of the edges or seam 40', laterally outwardly and upwardly, convexly curved upper inner edges 42 extending laterally and upwardly from the upper ends of the central edges or seam 40' and laterally outwardly convexly curved upper outer edges 43 extending between the lateral outer ends of the edges 41 and 42.

The lower edges 41 of the cups extend from the central portion of the panel 10, substantially midway between the upper and lower limits thereof, laterally outwardly in a downwardly and thence upwardly curved line across the front surfaces of the related left and right portions of the panel 10, in vertical spaced relationship between their related edges 16" and 23' of the panel 10 and continue outwardly and upwardly across their related seams 12 to terminate at the upper forward portions of their related side panels 11, as clearly illustrated in FIGS. 1 and 2 of the drawings.

The lower edges 41 of the cups are suitably seamed and are fixed to the band by stitching 44. The stitching 44 extends from the lateral outermost extremities of the cup edges to near proximity to, but spaced a limited distance laterally outward from and below the lower end of the central seam as indicated by the reference characters X and Y in FIG. 1 of the drawings, whereby the cup assembly can be advantageously folded forwardly and downwardly from its normal up or closed position, as shown in FIGS. 1 and 4 of the drawings, to an open position, as shown in solid lines in FIG. 2 and in dotted lines in FIG. 4 of the drawings, when the brassiere is worn and so as to provide convenient access to the interior of the cups.

The unsecured inner portions of the bottom edges and the inner and outer upper edges 42 and 43 of the cups are suitably hemmed or provided with finished bindings, as shown in the drawings.

The upper end of the central vertical seam normally terminates adjacent and immediately forward of the apical center of the band 10. The apical central portion of the band and adjacent portion of the cup assemblies are normally releasably secured together to substantially maintain the cup assembly in its normal up or closed position by suitable releasable fastening means F which means can, for example, include matting patches of VELCRO fixed to the opposing front and rear surfaces of the band and cup assemblies VELCROW is the tradename for that form of coupling means comprising matting fabric sheets with interengageable hook and eye nap.

The brassiere next includes shoulder strap means comprising a pair of support straps 50 each related to one side or half of the front panel 10 and each having one end fixed to the upper end of its related side seam 12 and the other end attached to the apical center point of the panel. The support straps are longer than the distance between their points of joinder with the band or panel and extend laterally across their adjacent related portions of the body of the wearer in a curve or arch which normally substantially circumbscribes what would be a desirable line of definition of the upper portion of a wearer's breast.

Each strap 50 can be made longitudinally adjustable and is preferably provided with a longitudinally extensible elastic section at one of its ends (not shown) to impart desirable adjusting capability and flexibility into the construction.

The shoulder strap means next includes a slidable metal loop 51 on each strap 50, a pair of laterally spaced frontwardly and rearwardly extending, arched, shoulder straps 52, to extend over the wearer's shoulders and each with a lower rear end fixed to the rear end of a related side panel 11 of the band B and an upper front end coupled with the loop 51 on its related strap 50. The straps 52 are preferably longitudinally adjustable, in accordance with common practices, and the means provided to couple them to the loops 51 is shown as including a short strap sections 53 engaged with the loops 51 and carrying rings 54 through which doubled portions of the principal sections of the straps are engaged.

The shoulder strap means described above serves to provide vertical support for each side or half of the front panel 10 and each side panel 11 of the band B, at each end of the noted portions of the panel 10 and of the panels 11.

Particularly, the shoulder strap means hold up and support the center of the panel 10 from points spaced above and laterally outward of the opposite sides of said center and support the outer sides of the panel 10 from the top of the vertical seams 12 defining said outer sides and from said points which occur above and are spaced laterally inward of the upper ends of the seams 12.

The shoulder strap means next and finally includes hanger hooks 55 carried by the strap sections 53 and hanger loops 56 of ribbon or strap fixed to the cups, at the junctions of the edges 42 and 43 and releasably engaged with the hooks 55 to hold and releasably maintain the upper portions of the cups in the normal up position, as clearly illustrated.

Finally, the brassiere provided by the present invention includes one or two back panels P related to the cup or to the cups with which a prosthetic breast is to be related.

In the case illustrated, I have shown the brassiere provided with one panel P related to the right hand cup C whereby the brassiere is established for use by a wearer whose right breast has been removed. It will be apparent and it is to be understood that a panel P could also be related to the left hand cup in the event the wearer has had both breasts removed or could be related to the left hand cup alone in the event only the wearer's left breast has been removed.

In practice, the brassiere can be produced with both left and right panels P and each panel P can be separately secured to the remainder of the structure, as will hereafter be described by distinct stitching; for example, by a stitching with heavier and/or color-coded thread, whereby one of the panels can be removed from the structure, as by pulling or stripping the noted stitching therefrom and to thereby adapt the brassiere for the user who has had but one breast removed. Such practice makes possible the manufacture of one, complete, convenient to stock, brassiere structure suitable for double mastectomy users and which can be simply, easily and quickly modified for either left or right side single mastectomy users, by simple removal of one panel P.

The panels P are substantially flat, vertical flexible panels of soft fabric with front and rear surfaces 60 and 61 and occur rearward of their related cups and their related portions of the front panel 10 in overlying and closing relationship with the rear of the cups.

The panels P preferably correspond in front vertical plane configuration with the normal front vertical plane configuration of their related cups, though they might be made a little larger or smaller in such configuration without departing from the spirit of my invention.

In practice, the edge portions of the panels P or of the panel P which occur adjacent the rear surface of the panel 10 are hemmed and are stitched to the panel by stitching 62. The above noted edge portions preferably register with corresponding edges of the cups, at the front surface of the panel 10 and the stitching 62 extends completely through the resulting laminate structure to establish a secure integrated structure. The other or remaining edges of the panel P are suitably hemmed or provided with finished binding, as illustrated in the drawings.

The fabric of the panels P is preferably a rather thick, soft, non-irritating fabric which offers a limited amount of padding and which will establish a smooth front surface when engaged over irregular scar tissue or the like resulting from the mastectomy and is preferably a heat insulating material which readily breathes or allows for circulation of air whereby discomforting and undesirably heat and perspiration is not subject to being generated as a result of the close juxtapositioning of a prosthesis against the wearer's body. In practice, the panels P can be established of thermal cotton fabric such as is commonly used in establishing thermo undergarments.

When the brassiere that I provide is worn and in use, the panel P overlies the area of the wearer's chest cage from which a breast has been removed and overlies and closes the open rear side of the cup C related to it. The portion of the front panel which occurs between the panel P and cup C cooperates with the forwardly and upwardly extending lower portion of the cup which occurs forward of the panel 10 to define a transversely extending, upwardly opening recess, indicated by the reference character R, in which a prosthesis 70 can be engaged and seated in supported relationship.

The prosthesis 70 is soft and sufficiently formable or moldable so that its lower seated and supported within and by the recess R substantially conforms to the configuration of the recess, and in substantially the same manner that the lower portion of a real or natural breast would conform and be molded in and by that recess and/or as the natural breast of the wearer, engaged in the opposite recess R' defined by the panel 10 and other cup C is molded and supported.

The above molding and supporting function is extremely important since it assures molding and supporting the lower portion of the prosthesis and the wearer's natural or remaining breast in a like and symmetrical manner.

The portions of the cups C above the recesses R and R' mold and contain the upper forward portions of the prosthesis and the breast or the two prostheses in the case of a double mastectomies in a desired and uniform or symmetrical manner.

The portion of the panel or panels P above the panel 10 and rearward of the cup or cups C close the open rear of the cup or cups establish a protective barrier between the body of the wearer and the prostheses and adjacent shoulder strap means. They further serve to retain and prevent the prostheses from dropping, shifting or otherwise migrating downwardly between the brassiere and the body.

The U-shaped springs in the panel 10 and related to each cup C prevent their related portions of the panel 10 from collapsing, folding or rolling under the weight of the prostheses. Maintaining the side of the recess R defined by the panel 10 spread and in proper form or shape, assures maintenance of the recesses R and R' in their designed form or shape.

In the case of a real or natural breast, the U-shaped spring of my invention that would be related to such a breast, applies a lifting bias at the lower breast line (the line of joinder between the breast and the body). Such lifting bias along the noted breast line assured and maintains proper dispositioning of the lower portion of the breast in the recess R' and creates a situation wherein the weight and mass distribution of the portion of the breast in the recess R' is similar to the weight and mass distribution of the portion of the prostheses in the recess R', whereby the breast and the prostheses are supported and molded in a symmetrical and attractive manner and such that it cannot be determined by simple observation under normal circumstances which cups contain the prosthesis and the natural breast.

The prosthesis 70, shown in the drawing, includes a flexible plastic bladder 71 in the general shape of the breast it is to be substituted for. The bladder is filled with water or a jelly-like fluid F and is enclosed in a soft, flexible and attractive fabric envelope 70. This prosthesis is only illustrative of one common form of prosthesis that can be advantageously used in combination with my new brassiere.

In practice and operation, the brassiere is first engaged on the body of the wearer in a common or normal fashion, with the hanger hooks and loops 55 and 56 and with the fastening means F previously or subsequently disengaged.

With the brassiere thus engaged on the wearer and conditioned as above noted, the upper portions of the cup assembly are folded forwardly and downwardly to open and provide free access to the recesses R and R'. In the case of a single mastectomy, the natural breast of the wearer is urged forwardly over and in supported engagement with its related edge 23' of the panel 10 and into supported and molded engagement with the recess R'; whereupon the cup C related thereto can be returned to its up or normal position and the hanger loop 56 thereof engaged with the hanger hook 55 related thereto, whereby the breast is contained, supported and molded as desired. Thereafter, the prosthesis 70 is manually deposited and oriented in the recess R and the pocket C related thereto is returned to its normal position and the hanger hook and loop related thereto are made up.

When the structure is in the condition set forth above, the central portion of the cup assembly is still free and unsecured and sufficient access to the interior of the cups is available for convenient minor and final manual adjustment of both the breast and the prosthesis 70. After such final adjustments are made, the central portion of the cup assembly is urged upwardly and rearwardly toward the center of the front panel 10 and the coupling means F is made up, completing the putting on and/or application of the structure.

In the case of double mastectomies, it will be apparent that substantially the same proceeding is followed.

Having described only one preferred form and carrying out of my invention, I do not wish to be limited to the specific details herein set forth, but wish to reserve to myself any modifications and/or variations that might appear to those skilled in the art and which fall within the scope of the following claims.

I claim:

1. A prosthesis and breast supporting brassiere comprising a body-encircling band structure having rear ends with interengageable means and adapted to be joined at the back of the user and having a front portion defining and provided with a pair of laterally spaced, laterally extending upwardly opening breast and prosthesis receiving and supporting pockets, separate means for providing equalized vertical support for each of said pockets including a shoulder strap having a rear end attached to the rear end portion of the band related to the pocket and a front end portion at the front of the user and defining a loop and a second strap having ends attached to the upper edge of the band at the opposite ends of the pocket and extending upwardly into sliding engagement through said loop, resilient means carried by the portions of the band adjacent each pocket constantly operative to apply a vertical spreading bias in and through said portions of the band and applying a lifting bias along a portion of a line defined by the junction of the breast and body engaging surfaces of the band, a pair of laterally spaced substantially forwardly projecting, rearwardly opening semi-conical breast and prosthesis covering and forming cups, each arranged forward of one of said pockets and having substantially laterally outwardly and upwardly extending outer lower edge portions adjacent and fixed to related outer lower edge portions of the cup, laterally substantially inwardly and upwardly extending inner lower edge portions terminating adjacent an upper edge of the band at the center thereof and having substantially upwardly convergent upper inner and outer edge portions extending from the inner and outer ends of the pocket toward the front end portions of the shoulder strap related thereto, releasable coupling means between the junction of said upper inner and outer edge portions of each cup and the shoulder strap related thereto, and a substantially flat vertical rear panel corresponding in general vertical rear plane configuration with each cup with which a prosthesis is related and positioned rearward of the cup and its related portions of the band in overlying relationship with the open rear of the cup and having edge portions adjacent the band fixed to the band, the upper and lower inner edge portions of the cups converge and are joined adjacent the upper central edge portion of the band and further including releasable fastening means between the central portion of the band and the area or joinder between the cups.

2. A prosthesis and breast supporting brassiere comprising a body-encircling band structure having rear ends with interengageable means and adapted to be joined at the back of the user and having a front portion defining and provided with a pair of laterally spaced, laterally extending upwardly opening breast and prosthesis receiving and supporting pockets, separate means for providing equalized vertical support for each of said pockets including a shoulder strap having a rear end attached to the rear end portion of the band related to the pocket and a front end portion at the front of the user and defining a loop and a second strap having ends attched to the upper edge of the band at the opposite ends of the pocket and extending upwardly into sliding engagement through said loop, resilient means carried by the portions of the band adjacent each pocket constantly operative to apply a vertical spreading bias in and through said portions of the band and applying a lifting bias along a portion of a line defined by the junction of the breast and body engaging surfaces of the band, a pair of laterally spaced substantially forwardly projecting, rearwardly opening semi-conical breast and prosthesis covering and forming cups, each arranged forward of one of said pockets and having substantially laterally outwardly and upwardly extending outer lower edge portions adjacent and fixed to related outer lower edge portions of the cup, laterally substantially inwardly and upwardly extending inner lower edge portions terminating adjacent the upper edge of the band at the center thereof and having substantially upwardly convergent upper inner and outer edge portions extending from the inner and outer ends of the pocket toward the front end portions of the shoulder strap related thereto, releasable coupling means between the junction of said upper inner and outer edge portions of each cup and the shoulder strap related thereto, and a substantially flat vertical rear panel corresponding in general vertical rear plane configuration with each cup with which a prosthesis is related and positioned rearward of the cup and its related portions of the band in overlying relationship with the open rear of the cup and having edge portions adjacent the band fixed to the band, the forward portion of the band comprises two normally flat vertical plies of fabric, the upper and lower laterally extending edges of which are stitched and bound, said pockets are defined by laterally extending normally forwardly and upwardly inclined members adjacent opposite side portions of the forward portion of the band with forwardly laterally outwardly and thence inwardly curved upper edges in substantially common planes with their adjacent upper edge portions of the band and with laterally outwardly and downwardly and thence upwardly and outwardly curved lower edges fixed to their adjacent portions of the band on lines between the upper and lower edges thereof wherein said resilient means includes a resilient rod bent into a U-shaped form and disposed between the plies of the portions of the band with which it is related with its bend end portion in spaced relationship from and disposed toward the front center portion of the band and with its opposite leg portions extending laterally outwardly in seated substantially parallel relationship with the stitched and bound upper and lower edges of the band.

3. A brassiere as set forth in claim 2 wherein the upper and lower inner edge portions of the cups converge adjacent the upper central edge portion of the band and are joined and fixed together.

4. A brassiere as set forth in claim 3 which further includes releasable fastening means between the central portion of the band and the area of joinder between the cups.

* * * * *